US00PP11506P

United States Patent [19]

Dümmen

[11] Patent Number: Plant 11,506

[45] Date of Patent: Sep. 12, 2000

[54] NEW GUINEA IMPATIENS PLANT NAMED 'DUERIBLUSTAR'

[75] Inventor: Marga Dümmen, Rheinberg, Germany

[73] Assignee: Dummen Jungpflazenkulturen, Rheinberg, Germany

[21] Appl. No.: 09/105,364

[22] Filed: Jun. 26, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 8,430 10/1993 Keintzler ..... Plt./318

P.P. 9,338 10/1995 Dehan ..... Plt./318

*Primary Examiner*—Lynette R. F. Smith
*Assistant Examiner*—Wendy A. Baker
*Attorney, Agent, or Firm*—C. A. Whealy

[57] ABSTRACT

A new and distinct variety of New Guinea Impatiens plant named 'Dueriblustar', characterized by its dark pink petal color; freely flowering; dense and bushy plant habit; freely and basally branching plant habit; and dark green and non-variegated foliage.

1 Drawing Sheet

BACKGROUND OF THE INVENTION

The present invention relates to a new and distinct variety of New Guinea Impatiens plant, botanically known as *Impatiens hawkeri*, and hereinafter referred to by the name 'Dueriblustar'. The new variety is marketed under the trade name Red Fox Riviera Blue Star.

The new variety is a product of a planned breeding program conducted by the Inventor in Rheinberg, Germany. The objective of the breeding program is to develop New Guinea Impatiens that are freely branching; compact; early flowering; and that have desirable flower and leaf colors.

The new cultivar originated from a cross made by the Inventor of the proprietary New Guinea Impatiens seedling selection identified as code number K-09 as the male or pollen parent with an unidentified proprietary New Guinea Impatiens seedling selection as the female or seed parent.

'Dueriblustar' was discovered and selected in 1995 by the Inventor as a single flowering plant within the progeny of the stated cross in a controlled environment in Rheinberg, Germany.

Asexual reproduction of the new variety by terminal cuttings taken at Rheinberg, Germany, has shown that the unique features of this new variety are stable and reproduced true to type in successive generations of asexual reproduction.

BRIEF SUMMARY OF THE INVENTION

The following traits have been repeatedly observed and are determined to be the unique characteristics of 'Dueriblustar'. These characteristics in combination distinguish 'Dueriblustar' as a new and distinct variety:

1. Dark pink petal color.
2. Freely flowering.
3. Dense and bushy plant habit.
4. Freely and basally branching plant habit.
5. Dark green and non-variegated foliage.

In side-by-side comparisons conducted by the Inventor in Rheinberg, Germany, plants of the new New Guinea Impatiens are more freely branching, more uniform and have more attractive flower color contrast than plants of the male parent, selection number K-09. Compared to plants of the female parent, the new New Guinea Impatiens is more uniform and differs in flower color.

The new variety can be compared to the commercial cultivar Duesarabande (not patented). However, in side-by-side comparisons conducted by the Inventor in Rheinberg, Germany, plants of the new variety are more compact, have more round flowers and more attractive flower color contrast.

BRIEF DESCRIPTION OF THE PHOTOGRAPH

The accompanying colored photograph illustrates the overall appearance of the new variety, showing the colors as true as it is reasonably possible to obtain in colored reproductions of this type. The photograph comprises a side perspective view of a typical plant of 'Dueriblustar'. Flower and foliage colors may appear lighter than actual colors due to light reflectance.

DETAILED BOTANICAL DESCRIPTION

Plants of 'Dueriblustar' have not been observed under all possible environmental conditions. The phenotype may vary somewhat with variations in environment such as temperature, daylength and light intensity, without, however, any variance in genotype. The following observations and measurements describe plants grown in 12-cm containers during the spring in Rheinberg, Germany, under commercial practice in a glass-covered greenhouse with day of about 22° C., night temperatures about 18° C. and light levels about 42.5 thousand lux.

In the following description, color references are made to The Royal Horticultural Society Colour Chart except where general terms of ordinary dictionary significance are used.

Botanical classification: *Impatiens hawkeri* 'Dueriblustar'.
Parentage:

*Male, or pollen, parent*—*Impatiens hawkeri* seedling selection, code number K-09.

*Female, or seed, parent*.—Unidentified *Impatiens hawkeri* seedling selection.

Propagation:

*Type cutting*.—Terminal cuttings.

*Time to initiate roots*.—Summer: About 10 days at 22° C. Winter: About 12 days at 22° C.

*Time to develop roots*.—Summer: About 21 days at 22° C. Winter: About 26 days at 22° C.

*Rooting habit*.—Fine, freely branching.

Plant description:

*General appearance*.—Rounded; full, dense and bushy; very freely and basally branching; upright and spreading; rapid growth rate; suitable for 10 to 16-cm pots.

*Plant height*.—About 23 cm from soil level to top of plant plane.

*Lateral branches*.—Quantity: About 24. Length: About 14 cm. Diameter: About 8 mm. Internode length: About 3.5 cm. Color: 146C.

*Foliage description*.—Quantity of leaves per lateral branch: About 50. Shape: Elliptic with acuminate tip and attenuate base. Length: About 10.5 cm. Width: About 3.7 cm. Texture: Smooth, glabrous. Margin: Serrulate. Color: Young foliage, upper surface: 147A. Young foliage, lower surface: 59A. Mature foliage, upper surface: 147A. Mature foliage, lower surface: 59A. Veins, upper surface: 59A. Veins, lower surface: 136A. Petiole: Length: About 2.6 cm. Diameter: About 2.5 mm. Color: 136C.

Flower description:

*Flowering habit*.—Freely flowering. Flowers not persistent.

*Natural flowering season*.—Year-round. Plants flower about 7.5 weeks after planting.

*Flowers borne*.—Flower buds develop in apical leaf axils. Open flowers are displayed above the foliage.

*Quantity of inflorescences*.—Freely flowering, usually about 135 flower buds and open flowers per plant.

*Flower shape*.—Rounded.

*Flower diameter*.—About 5.3 cm.

*Petals*.—Shape: Obcordate with emarginate apex and acute base. Quantity, arrangement: 5 petals overlapping. Aspect: Flat. Length: About 2.6 cm. Width: About 3.5 cm. Texture: Smooth, satiny, and glabrous. Margin: Entire. Color: When opening, upper surface: 80B with 74A central stripe and upper petal center; 61A at base. When opening, lower surface: 74A at center; 80B at margin; 61A at base. Fully opened, upper surface: 78A to 78B; central stripe and upper petal center, close to 74A with tinge of orange; 61A at base. Fully opened, lower surface: 74A at center; 80B at margin; 61A at base.

*Peduncle*.—Angle: Erect. Strength: Slender, but moderate. Length: About 6.2 cm. Color: 137D.

*Flower bud*.—Shape: Ovoid with spur. Length: About 1.9 cm. Diameter: About 1.2 cm. Color: 59B/59C.

*Spur*.—Shape: Needle-shaped, curved at end. Length: About 4.5 cm. Color: 160B.

*Reproductive organs*.—Androecium: Stamen number: 5. Anther shape: Oval. Anther size: About 5.5 mm. Anther color: 49C. Pollen color: 20D. Amount of pollen: Abundant. Gynoecium: Pistil length: About 5 mm. Stigma color: 131A. Ovary color: 141B.

Disease resistance: Resistance to pathogens common to New Guinea Impatiens has not been observed.

Seed development: Seed production has not been observed.

It is claimed:

1. A new and distinct variety of New Guinea Impatiens plant named 'Dueriblustar', as illustrated and described.

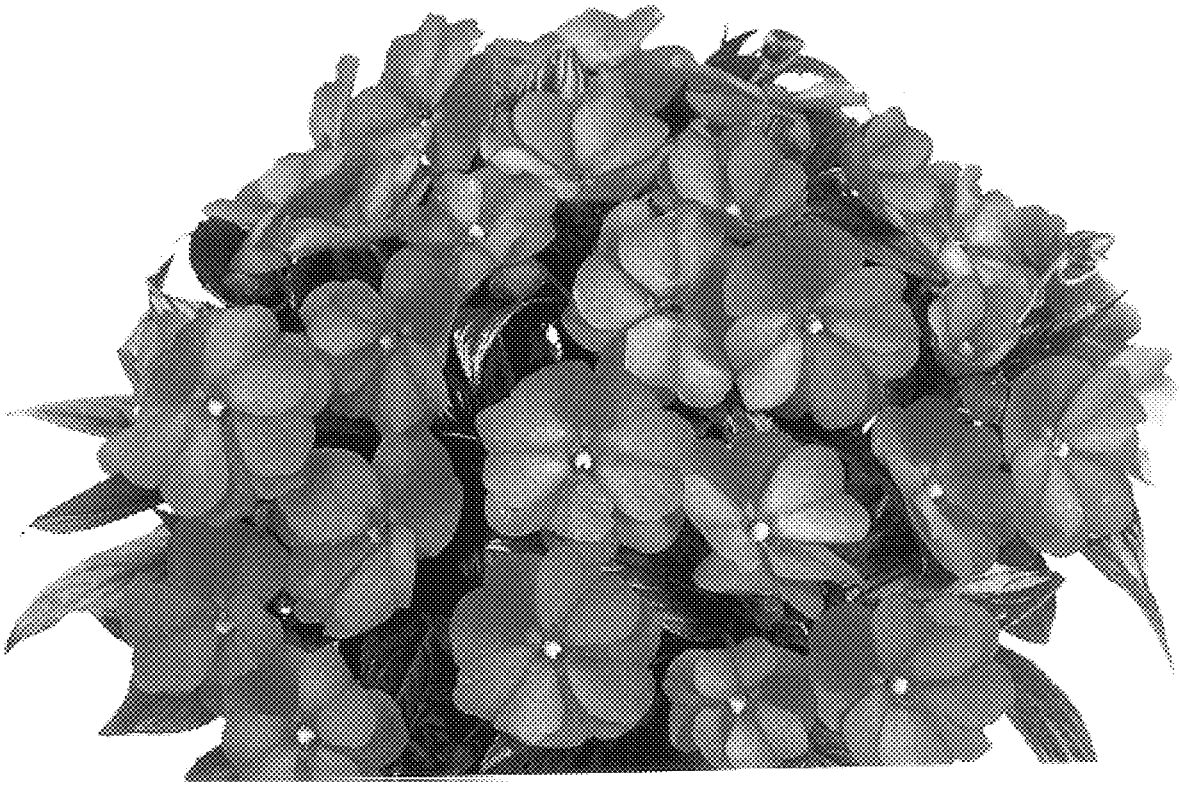

* * * * *